United States Patent
Lau (10) Patent No.: US 9,890,405 B2
(45) Date of Patent: Feb. 13, 2018

(54) RECOMBINANT BACTERIAL CELLS PRODUCING (S)-2-AMINO-6-HYDROXYPIMELATE

(71) Applicant: BioAmber Inc., Plymouth, MN (US)

(72) Inventor: Man Kit Lau, Minneapolis, MN (US)

(73) Assignee: BIOAMBER INC., St. Paul, MN (US)

(*) Notice: Subject to any disclaimer, the term of this patent is extended or adjusted under 35 U.S.C. 154(b) by 0 days.

(21) Appl. No.: 14/419,310

(22) PCT Filed: Aug. 21, 2013

(86) PCT No.: PCT/US2013/055950
§ 371 (c)(1),
(2) Date: Feb. 3, 2015

(87) PCT Pub. No.: WO2014/031724
PCT Pub. Date: Feb. 27, 2014

(65) Prior Publication Data
US 2015/0203879 A1    Jul. 23, 2015

Related U.S. Application Data

(60) Provisional application No. 61/692,389, filed on Aug. 23, 2012.

(51) Int. Cl.
| | | |
|---|---|---|
| *C12P 13/00* | (2006.01) | |
| *C12N 9/04* | (2006.01) | |
| *C12N 9/88* | (2006.01) | |
| *C12N 9/06* | (2006.01) | |
| *C12N 9/02* | (2006.01) | |
| *C12N 9/10* | (2006.01) | |
| *C12N 9/00* | (2006.01) | |
| *C12P 13/04* | (2006.01) | |
| *C12N 9/16* | (2006.01) | |

(52) U.S. Cl.
CPC ............ *C12P 13/001* (2013.01); *C12N 9/001* (2013.01); *C12N 9/0006* (2013.01); *C12N 9/0008* (2013.01); *C12N 9/0016* (2013.01); *C12N 9/1096* (2013.01); *C12N 9/13* (2013.01); *C12N 9/16* (2013.01); *C12N 9/88* (2013.01); *C12N 9/93* (2013.01); *C12P 13/005* (2013.01); *C12P 13/04* (2013.01)

(58) Field of Classification Search
None
See application file for complete search history.

(56) References Cited

U.S. PATENT DOCUMENTS 8,404,465 B2    3/2013    Baynes

FOREIGN PATENT DOCUMENTS

| EP | 0834559 | 4/1998 |
|---|---|---|
| WO | WO 2004/013341 | 2/2004 |
| WO | WO 2010/068944 | 6/2010 |
| WO | WO 2011/130378 | 10/2011 |

OTHER PUBLICATIONS

Hsu et al., "Addition of Autotrophic Carbon Fixation Pathways to Increase the Theoretical Heterotrophic Yield of Acetate", The Fourth International Conference on Computational Systems Biology (ISB2010), Suzhou, China, Sep. 9-11, 2010, pp. 314-322.*
Kizer et al. Appl Environ Microbiol. May 2008;74(10):3229-41.*
Prather et al. Curr Opin Biotechnol. Oct. 2008;19(5):468-74.*
Berges et al., "Studies on the Active Site of Succinyl-coa: Tetrahydrodipicolinate Nsuccinyltransferase, Characterization using Analogs of Tetrahydrodipicolinate," Journal of Biological Chemistry, vol. 261, No. 14, pp. 6160-6197, May 1986.
Yong Gao, "Synthesis of Diarninopimelic Acid (DM) and Analogues; Mechanistic Studies of DAP Aminotransferase, Epimerase and Dehydrogenase," pp. 1-166, Jan. 1998, http://www.collectionscanada.gc.ca/obj/s4/f2/dsk2/ftp02/NQ34768.pdf.
Liang et al., "Increased Production of Succinic Acid in *Escherichia coli* by Overexpression of Malate Dehydrogenase," Biotechnol. Lett., 33:2439-2444, Jul. 2011.
Lloyd-Davies, et al., "Glycerylphosphorylcholine Phosphodiesterase in Rat Liver" Biochem. J., 1972, 127, pp. 357-368.
Savijoki et al., "Molecular Genetic Characterization of the L-Lactate Dehydrogenase Gene (IdhL) of Lactobacillus helveticus and Biochemical Characterization of the Enzyme" Applied and Environmental Microbiology, Jul. 1997, vol. 63, No. 7, pp. 2850-2856.
Kohn et al., "Tartaric Acid Metabolism V. Crystalline Tartrate Dehydrogenase" J. Biol. Chem., May 1968, vol. 243, No. 10, pp. 2479-2485.
Neumann et al., "On a Non-Pyridine Nucleotide-Dependent 2-OXO-Acid Reductase of Broad Substrate Specificity from Two Proteus Species" Federation of European Biochemical Societies, Feb. 1984, vol. 167, No. 1, pp. 29-32.
Taguchi et al., D-Lactate Dehydrogenase is a Member of the D-Isomer-Specific 2-Hydroxyacid Dehydrogenase Family, J. Biol. Chem., Jul. 1991, vol. 266, No. 19, pp. 12588-12594.

(Continued)

*Primary Examiner* — Christian Fronda
(74) *Attorney, Agent, or Firm* — Baker & Hostetler LLP (57) ABSTRACT

A chemical having the formula (S) 2-amino-6-hydroxypimelate. (S)-2-amino-6-hydroxypimelate can be made using a method comprising culturing a cell comprising an exogenous nucleic acid sequence encoding an enzyme that catalyzes the substrate to product conversion of (S)-2-amino-6-oxopimelate to (S)-2-amino-6-hydroxypimelate and separating the (S)-2-amino-6-hydroxypimelate. The cell may be a recombinant microorganism for producing aminocaproic acid or hexamethylenediamine from (S)-2-amino-6-hydroxypimelate comprising at least one exogenous nucleic acid sequence that expresses at least one polypeptide with substrate preference for homolysine, and amino acid decarboxylase with substrate preference for alpha-aminopimelate.

5 Claims, 1 Drawing Sheet

(56) References Cited

OTHER PUBLICATIONS

Chambellon et al., "The D-2-Hydroxyacid Dehydrogenase Incorrectly Annotated PanE is the Sole Reduction System for Branched-Chain 2-Keto Acids in Lactococcus Lactis" J. Bacteriol., Feb. 2009, vol. 191, No. 3, pp. 873-881.
Suda et al., "Purification and Properties of α-ketoadipate Reductase, a Newly Discovered Enzyme from Human Placenta", Abstract, Archives of Biochemistry and Biophysics, Oct. 1976, vol. 176, Issue 2, pp. 610-620.

* cited by examiner

RECOMBINANT BACTERIAL CELLS PRODUCING (S)-2-AMINO-6-HYDROXYPIMELATE

FIELD

This disclosure relates to recombinant microorganisms and methods of producing intermediates useful for producing hexamethylenediamine and aminocaproic acid, as well as methods for producing hexamethylenediamine and aminocaproic acid.

BACKGROUND

Crude oil is the number one starting material for the synthesis of key chemicals and polymers. As oil becomes increasingly scarce and expensive, biological processing of renewable raw materials in the production of chemicals using live microorganisms or their purified enzymes becomes increasingly interesting. Biological processing, in particular, fermentations have been used for centuries to make beverages. Over the last 50 years, microorganisms have been used commercially to make compounds such as antibiotics, vitamins, and amino acids. However, the use of microorganisms for making industrial chemicals has been much less widespread. It has been realized only recently that microorganisms may be able to provide an economical route to certain compounds that are difficult or costly to make by conventional chemical means.

SUMMARY

The engineered biosynthetic pathways, such as those described herein for making intermediates to HMDA and ACA, as well as HMDA and ACA (hereinafter "Products") are desirable and can provide economically and/or environmentally favorable alternatives to prior published pathways and petrochemical derived products. One of ordinary skill in the art will appreciate that the selection of a particular host, an engineered biosynthetic pathway and enzymes within that selected engineered biosynthetic pathway will depend upon many factors, including for example, geographic location of production, the variety of feedstock available, and the prevailing regulatory environment. Hence, while technical factors such as yield of product based on carbon input can be important, they are not solely determinative for allowing industries to shift away from petrochemical derived sources of products to renewable sources, such as described herein.

Described herein are useful compounds such as (S) 2-amino-6-hydroxypimelate, HMDA and ACA. These compounds are useful for the production of polymers from carbohydrate feedstocks. These compounds can be made at least partially from recombinant microorganisms that are also described herein. Some of the recombinant microorganisms described herein are engineered to express one or more enzymes that catalyze a substrate to product conversion comprising (S)-2-amino-6-oxopimelate to (S)-2-amino-6-hydroxypimelate. Additional microorganisms described herein express one or more enzymes that catalyze substrate to product conversions selected from (S)-2-amino-6-hydroxypimelate to (S)-2-amino 6-hydroxypimeloyl-CoA, (S)-2-amino 6-hydroxypimeloyl-CoA to (S)-1-amino-1-carboxy-2-hexenoyl-CoA, (S)-1-amino-1-carboxy-2-hexenoyl-CoA to (S)-2-aminopimeloyl-CoA, (S)-2-aminopimeloyl-CoA to 2-amino-7-oxoheptanoate, 2-amino-7-oxoheptanoate to homolysine, homolysine to hexamethylenediamine, (S)-2-aminopimeloyl-CoA to alpha-aminopimelate, and alpha-aminopimelate to (S)-2-aminopimeloyl-CoA, alpha-aminopimelate to aminocaproic acid, (S)-1-amino 1-carboxy-2-hexenoyl-CoA to (S)-2-amino-5-heptenedioate, (S)-2-amino-5-heptenedioate to (S)-1-amino 1-carboxy-2-hexenoyl-CoA, (S)-2-amino-6-hydroxypimelate to (S)-2-amino-5-heptenedioate, and (S)-2-amino-5-heptenedioate to alpha-aminopimelate.

Methods are also provided for making products via culturing the recombinant microorganisms and separating the products from the fermentation broth. Such methods include methods of making (S)-2-amino-6-hydroxypimelate, ACA, HMDA, and combinations thereof.

The recombinant microorganisms used in the methods described herein can express one or more exogenous nucleic acid sequences that encode one or more polypeptides having activities selected from 2-oxo-acid/reductase, dehydratase, CoA transferase, enoate reductase, acrylyl-CoA reductase, acyl-CoA dehydrogenase, CoA transferases, CoA ligase, thioesterase/hydrolase, aldehyde dehydrogenase, acylating dehydrogenase, amine dehydrogenase, transaminase, amino acid decarboxylase with substrate preference for homolysine, and amino acid decarboxylase with substrate preference for alpha-aminopimelate.

DESCRIPTION OF THE FIGURE

FIG. 1 shows the chemical structures of reactants and products in the pathways. The letters adjacent to the arrows correspond to the reactions described in the text and the accompanying Tables. The numbers adjacent to the arrows correspond to the Table number that describes the enzyme classification number (E.C.) associated with enzymes that can be used for the indicated reaction. In some instances more than one reaction can be accomplished using the same enzyme and, therefore, the same Table is indicated for multiple steps. For example, the enzymes listed in Table 7 can be used for both the G and the $G^1$ reaction.

DETAILED DESCRIPTION

Described herein are recombinant microorganisms for producing (S)-2-amino-6-hydroxypimelate, hexamethylenediamine (HMDA), 6-aminocaproic acid (ACA) from (S)-2-amino-6-oxopimelate. These products are produced by diverting the lysine biosynthesis pathway of the host organism. One of ordinary skill in the art will appreciate the methods of increasing lysine production in microorganisms can be used in combination with the pathways provided herein to increase production of intermediates within the pathways, as well as ACA and HMDA. Methods of increasing lysine production are known in the art and can be accomplished through fermentation techniques, genetic engineering and combinations thereof. Examples of methods of increasing lysine production from microorganisms are described in the following publications WO1996041871 and WO2004013341.

As used herein, the following terms and phrases shall have the meanings set forth below. Unless defined otherwise, all technical and scientific terms used herein have the same meaning as commonly understood to one of ordinary skill in the art.

The singular forms "a," "an," and "the" include plural reference unless the context clearly dictates otherwise.

The terms "comprise" and "comprising" are used in the inclusive, open sense, meaning that additional elements may be included.

The terms "host cell" and "microorganism" are used to describe the cell into which the altered nucleic acid sequence has been introduced. The altered nucleic acid sequence can be created by insertions of new nucleic acid sequences, deletions of base pairs, and combinations thereof.

The term "including" is used to mean "including but not limited to".

Figure 1:
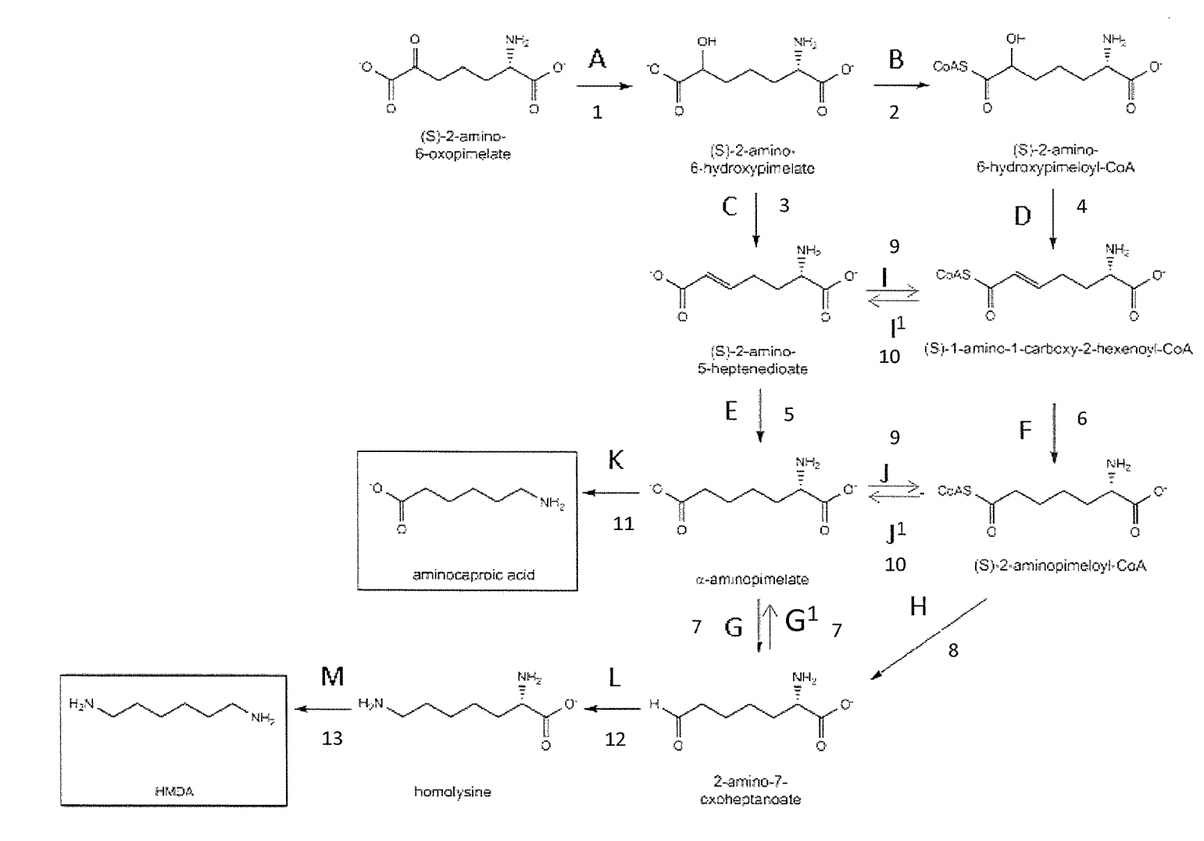

The term "product" refers to intermediates such as (S)-2-amino-6-hydroxypimelate, and (S)-2-amino-6-hydroxypimeloyl-CoA, as well as aminocaproic acid (ACA) and hexamethyldiamine (HMDA) shown in FIG. 1.

The term "alcohol" refers, for example, to an alkyl moiety in which one or more of the hydrogen atoms has been replaced by an —OH group. The term "primary alcohol" refers, for example to alcohols in which the —OH group is bonded to a terminal or chain-ending carbon atom, such as in 1-hexanol and the like. The term "secondary alcohol" refers, for example to alcohols in which the —OH group is bonded to a carbon atom that is bonded to one hydrogen atom and to two other carbon atoms, such as in 2-hexanol and the like. The term "tertiary alcohol" refers, for example to alcohols in which the —OH group is bonded to a carbon atom that is bonded to three other carbon atoms.

The term "amine" refers, for example, to an alkyl moiety in which one or more of the hydrogen atoms has been replaced by an —NH2 group.

The term "carbonyl compound" refers, for example, to an organic compound containing a carbonyl group, C=O, such as, for example, aldehydes, which have the general formula RCOH; ketones, which have the general formula RCOR'; carboxylic acids, which have the general formula RCOOH; and esters, which have the general formula RCOOR'.

The term "codon optimization" or "codon-optimized" refers to modifying the codon content of a nucleic acid sequence without modifying the sequence of the polypeptide encoded by the nucleic acid to enhance expression in a particular host cell. In certain embodiments, the term is meant to encompass modifying the codon content of a nucleic acid sequence as a means to control the level of expression of a polypeptide (e.g., to either increase or decrease the level of expression).

The term "metabolic pathway" refers to a series of two or more enzymatic reactions in which the product of one enzymatic reaction becomes the substrate for the next enzymatic reaction. At each step of a metabolic pathway, intermediate compounds are formed and utilized as substrates for a subsequent step. These compounds may be called "metabolic intermediates." The products of each step are also called "metabolites."

The terms "nucleotide sequence", "nucleic acid sequence" and "genetic construct" are used interchangeably and mean a polymer of RNA or DNA, single- or double-stranded, optionally containing synthetic, non-natural or altered nucleotide bases. A nucleotide sequence may comprise one or more segments of cDNA, genomic DNA, synthetic DNA, or RNA. In a preferred embodiment, the nucleotide sequence is codon-optimized to reflect the typical codon usage of the host cell without altering the polypeptide encoded by the nucleotide sequence.

The term "organic molecule" refers, for example, to any molecule that is made up predominantly of carbon and hydrogen, such as, for example, alkanes. Organic molecules of interest, include intermediates such as (S)-2-amino-6-hydroxypimelate, as well as aminocaproic acid (ACA) and hexamethyldiamine (HMDA) as shown in FIG. 1.

The terms "polypeptide," "protein" and "peptide," which are used interchangeably herein, refer to a polymer of amino acids, including, for example, gene products, naturally-occurring proteins, homologs, orthologs, paralogs, fragments, and other equivalents, variants and analogs of the forgoing. The term "polypeptide having enzymatic activity" refers to any polypeptide that catalyzes a chemical reaction of other substances without itself being destroyed or altered upon completion of the reaction. Typically, a polypeptide having enzymatic activity catalyzes the formation of one or more products from one or more substrates. In some aspects of the invention, the catalytic promiscuity properties of some enzymes may be combined with protein engineering and may be exploited in novel metabolic pathways and biosynthesis applications. In some embodiments, existing enzymes are modified for use in organic biosynthesis.

The term "recombinant" or "genetically modified" as used herein refers to a host cell that contains an altered nucleic acid sequence that is not found in the wild type host cell. Recombinant host cells can have new metabolic capabilities or new metabolic pathways. As used herein the term genetically modified, with reference to microorganisms, refers to microorganisms having at least one genetic alteration not normally found in the wild type strain of the reference species. In some embodiments, genetically engineered microorganisms are engineered to express or overexpress at least one particular enzyme at critical points in a metabolic pathway, and/or to block the synthesis of other enzymes, to overcome or circumvent metabolic bottlenecks.

The term "sequence identity" is herein defined as a relationship between two or more amino acid (polypeptide or protein) sequences or two or more nucleic acid (polynucleotide) sequences, as determined by comparing the sequences. Usually, sequence identities or similarities are compared over the whole length of the sequences compared. In the art, "identity" also means the degree of sequence relatedness between amino acid or nucleic acid sequences, as the case may be, as determined by the match between strings of such sequences.

Preferred methods to determine identity are designed to give the largest match between the sequences tested. Methods to determine identity and similarity are codified in publicly available computer programs. Preferred computer program methods to determine identity and similarity between two sequences include BLASTP and BLASTN, publicly available from NCBI and other sources (BLAST Manual, Altschul, S., et al., NCBI NLM NIH Bethesda, Md. 20894). Preferred parameters for amino acid sequences comparison using BLASTP are gap open 11.0, gap extend 1, Blosum 62 matrix.

A Making Recombinant Microorganisms

As described in U.S. Pat. No. 8,404,465 (herein incorporated by reference in its entirety), 2-amino-6-oxopimelate (also referred to as α-amino ε-keto-pimelate or 2-amino-6-oxoheptanedioic acid) can be made by diversion of the lysine pathway. FIG. 3A from U.S. Pat. No. 8,404,465 in combination with the accompany text and accompanying enzyme descriptions provide particularly relevant information.

The products described herein can be made using recombinant microorganisms. Genetically engineered microorganisms can include exogenous polypeptides, and polynucleotides encoding such polypeptides. Such polypeptides can have enzymatic activity or an improved activity for a natural or unnatural substrate or have broad substrate specificity (e.g., catalytic promiscuity such as substrate promiscuity). In some instances, the enzymes involved in the production of the products are selected from 2-oxo-acid/reductase, dehydratase, CoA transferase, enoate reductase, acrylyl-CoA reductase, acyl-CoA dehydrogenase, CoA transferases, CoA ligase, thioesterase/hydrolase, aldehyde dehydrogenase, acylating dehydrogenase, amine dehydrogenase, transaminase, amino acid decarboxylase with substrate preference for homolysine, and amino acid decarboxylase with substrate preference for alpha-aminopimelate. In some embodiments, the reaction mechanism of the enzyme chosen from the relevant tables (see, Tables 1-13) may be altered to catalyze new reactions, to change, expand or improve substrate specificity. One should appreciate that if the enzyme structure (e.g. crystal structure) is known, enzymes properties may be modified by rational redesign (see US patent application US20060160138, US20080064610 and US20080287320). Modification or improvement in enzyme properties may arise from the introduction of modifications into a polypeptide chain that may, in effect, perturb the structure-function of the enzyme and/or alter its interaction with another molecule (e.g., association with a natural substrate versus an unnatural substrate). It is well known in the art that certain regions of a protein may be critical for enzyme activity, for example amino acids involved in catalysis and substrate binding domains, such that small perturbations to these regions will have significant effects on enzyme function. Some amino acid residues may be at important positions for maintaining the secondary or tertiary structure of the enzyme, and thus also produce noticeable changes in enzyme properties when modified. In some embodiments, the potential pathway components are variants of any of the foregoing. Such variants may be produced by random mutagenesis or may be produced by rational design for production of an enzymatic activity having, for example, an altered substrate specificity, increased enzymatic activity, greater stability, etc. Thus, in some embodiments, the number of modifications to an enzyme initially chosen from Tables 1-13 (hereinafter a parent enzyme) that produces a variant enzyme having the desired property may comprise one or more amino acids, 2 or more amino acids, 5 or more amino acids, 10 or more amino acids, or 20 or more amino acids, up to 10% of the total number of amino acids, up to 20% of the total number of amino acids, up to 30% of the total number of amino acids, up to 40% of the total number of amino acids making up the reference enzyme, or up to 50% of the total number of amino acids making up the reference enzyme.

Those skilled in the art will understand that the engineered pathways exemplified herein are described in relation to, but are not limited to, species specific genes and proteins and that the invention encompasses homologs and orthologs of such gene and protein sequences. Homolog and ortholog sequences possess a relatively high degree of sequence identity/similarity when aligned using methods known in the art. Such homologs or orthologs can suitably be obtained by means of any appropriate cloning strategy known to one skilled in the art. In some embodiments, useful polypeptide sequences have at least 30%, at least 45%, at least 60%, at least 75%, at least 85%, or at least 95% identity to the amino acid sequence of the reference enzyme of interest.

Aspects of the invention provide methods for designing and making engineered metabolic pathways. In some aspects of the invention, alternative pathways for making a product of interest from one or more available and sustainable substrates may be made in one or more host cells or microorganisms of interest. One of ordinary skill in the art will appreciate that the engineered pathway for making products may involve multiple enzymes and therefore the flux through the pathway may not be optimum for the production of the product of interest. Consequently, in some aspects of the invention, the carbon flux is optimally balanced by modulating the activity level of the pathway enzymes relative to one another. Examples of such modulation are provided throughout the application. As used herein the term "carbon flux" refers to the number of feedstock molecules (e.g. glucose) which proceed down the engineered pathway relative to competitive paths.

Host cells can be eukaryotic, prokaryotic, derived from a multicellular organism (e.g. cell line) cultured as a unicellular entity. Exemplary host cells include bacterial, yeast, insect or mammalian. Bacterial host cells can be selected from *Escherichia coli, Bacillus subtilis, Mycobacterium* spp., *M. tuberculosis*, or other suitable bacterial cells. Archaea host cells can be Methanococcus Jannaschii or Methanococcus Maripaludis or other suitable archaic cells. Yeast cells can be *Saccharomyces* species such as *S. cerevisiae, S. pombe, Picchia* species, *Candida* species such as *C. albicans*, or other suitable yeast species.

In some embodiments, a host cell may be selected for subsequent genetic modification because of its particular metabolic properties, its ability to utilize particular carbon sources, and its ability to live under certain conditions, such as for example at an acidic pH or at a high temperature. For example, if a selection or screen is related to a particular metabolic pathway, it may be helpful to use a host cell that has a related pathway. Such a host cell may have certain physiological adaptations that allow it to process or import or export one or more intermediates or products of the pathway. However, in other embodiments, a host cell that expresses no enzymes associated with a particular pathway of interest may be selected in order to be able to identify all of the components required for that pathway using appropriate sets of genetic elements and not relying on the host cell to provide one or more missing steps.

According to aspects of the invention, aerobic or anaerobic microorganisms are metabolically engineered. As used herein, an anaerobic organism is any organism that does not require oxygen for growth (i.e. anaerobic conditions), such as certain bacterial cells. Advantageously, the bacterial cell can be an *E. coli, C. glutamicum, B. flavum* or *B. lactofermentum* cell; these strains are currently being employed industrially to make amino compounds using bacterial fermentation processes. For example, *C. glutamicum* has been used extensively for amino acid production (e.g. L-glutamate, L-lysine, see Eggleging L et al., 2005, Handbook for *Corynebacterium glutamicum*. Boca Raton, USA: CRC Press).

The metabolically engineered cell of the invention is made by transforming a host cell with at least one nucleotide sequence encoding enzymes involved in the engineered metabolic pathways. Accordingly, aspects of the invention include nucleic acid sequences encoding the enzymes involved in the engineered metabolic pathways. In some embodiments, a metabolically engineered cell may express one or more polypeptides having an enzymatic activity necessary to perform the steps described throughout the description (see, FIG. 1). For example, a particular cell comprises one, two, three, four, five or more than five nucleic acid sequences with each one encoding a polypeptide necessary to perform the conversion of a reactant into a product. In some instances the product in turn becomes the reactant for a subsequent reaction in the pathway, see FIG. 1. Alternatively, a single nucleic acid molecule can encode one, or more than one, polypeptide. For example, a single nucleic acid molecule can contain nucleic acid sequences that encode two, three, four or even five different polypeptides. Nucleic acid sequences useful for the invention described herein may be obtained from a variety of sources such as, for example, amplification of cDNA sequence, DNA libraries, de novo synthesis, excision of genomic segments, etc. The sequences obtained from such sources may then be modified using standard molecular biology and/or recombinant DNA technology to produce nucleic acid sequences having the desired modifications. Exemplary methods for modification of nucleic acid sequences include for example, site directed mutagenesis, PCR mutagenesis, deletion, insertion, or substitution, or swapping portions of the sequence using restriction enzymes, optionally in combination with ligation, homologous recombination, site specific recombination or various combination thereof. In other embodiments, the nucleic acid sequence may be a synthetic nucleic acid sequence. Synthetic polynucleotide sequences may be produce using a variety of methods described in U.S. Pat. No. 7,323,320, and in copending application having Ser. No. 11/804,996 and in U.S. Patent Publication Nos. 2006/0160138, 2007/0269870, 2008/0064610, and 2008/0287320.

Methods of transformation for bacteria, plant, and animal cells are well known in the art. Common bacterial transformation methods include electroporation and chemical treatment.

In some embodiments, a genetically modified host cell is genetically modified such that it produces, when cultured in vitro in a suitable medium, the product of interest or an intermediate at a level of at least 0.1 g/l, at least 1 g/l, at least 10 g/l, at least 50 g/l, at least 100 g/l or at least 150 g/l. One of ordinary skill in the art will appreciate that intermediates can be produced, separated and used in subsequent chemical or enzymatic reactions to produce additional products. In these instances the intermediate is also referred to as a product. One should appreciate that the level of the metabolite of interest or its metabolic intermediates produced by a genetically modified host cell can be controlled in various ways. In some embodiments, the level of expression is controlled by the number of copies of the nucleic acid sequences encoding one or more enzymes involved in the engineered pathway that are contained in the host cell (e.g. high copy expression vector versus medium or low copy expression vectors, copies genomically introduced). Preferably, the nucleic acid sequences are introduced into the cell using a vector. Low copy expression vectors generally provide fewer than 20 vector copies per cell (e.g. from 1 to about 5, from 5 to about 10, from 10 to about 15, from 15 to about 20 copies of the expression vector per cell). Suitable low copy expression vectors for prokaryotic cells (e.g. *E. Coli*) include, but are not limited to pAYC184, pBeloBacll, pBR332, pBAD33, pBBR1MCS and its derivatives, pSC101, SuperCos (cosmid) and pWE15 (cosmid). Medium copy number expression vectors generally provide from about 20 to about 50 expression vectors copies per cell or form about 20 to 80 expression vectors copies per cell. Suitable medium copy expression vectors for prokaryotic cells (e.g. *E. Coli*) include, but are not limited to, pTrc99A, pBAD24 and vectors containing a CoIE1 origin of replication and its derivatives. High copy number expression vectors generally provide from about 80 to about 200 or more expression vector copies per cell. Suitable high copy expression vectors for prokaryotic cells (e.g. *E. Coli*) include, but are not limited to, pUC, PCV1, pBluescript, pGEM and pTZ vectors.

Aspects of the invention provide expression cassettes comprising a nucleic acid or a subsequence thereof encoding a polypeptide involved in the engineered pathway. In some embodiments, the expression cassette can comprise the nucleic acid operably linked to control sequences, such as a transcriptional element (e.g. promoter) and to a terminator. As used herein, the term "cassette" refers to a nucleotide sequence capable of expressing a particular gene if the gene is inserted so as to be operably linked to one or more regulatory sequences present in the nucleotide sequence. Thus, for example, the expression cassette may comprise a heterologous gene which is desired to be expressed in the host cell. In some embodiments, one or more expression cassettes may be introduced into a vector by known recombinant techniques. A promoter is a sequence of nucleotides that initiates and controls the transcription of a desired nucleic acid sequence by an RNA polymerase enzyme. In some embodiments, the promoter may be inducible. In other embodiment, promoters may be constitutive. Non limiting examples of suitable promoters for the use in prokaryotic host cells include a bacteriophage T7 RNA polymerase promoter, a trp promoter, a lac operon promoter and the like. Non limiting examples of suitable strong promoters for the use in prokaryotic cells include lacUV5 promoter, T5, T7, Trc, Tac and the like. Non limiting examples of suitable promoters for use in eukaryotic cells include a CMV immediate early promoter, a SV40 early or late promoter, a HSV thymidine kinase promoter and the like. Termination control regions may also be derived from various genes native to the preferred host.

In some embodiments, a first enzyme of the engineered pathway may be under the control of a first promoter and the second enzyme of the engineered pathway may be under the control of a second promoter, wherein the first and the second promoter have different strengths. For example, the first promoter may be stronger than the second promoter or the second promoter may be stronger than the first promoter. Consequently, the level of a first enzyme may be increased relative to the level of a second enzyme in the engineered pathway by increasing the number of copies of the first enzyme and/or by increasing the promoter strength to which the first enzyme is operably linked to relative to the promoter strength to which the second enzyme is operably linked to. In some other embodiments, the plurality of enzymes of the engineered pathway may be under the control of the same promoter. In other embodiments, altering the ribosomal binding site affects relative translation and expression of different enzymes in the pathway. Altering the ribosomal binding site can be used alone to control relative expression of enzymes in the pathway, or it can be used in concert with the aforementioned promoter modifications and codon optimization that also affects gene expression levels.

In an exemplary embodiment, expression of the potential pathway enzymes may be dependent upon the presence of a substrate that the pathway enzyme will act on in the reaction mixture. For example, expression of an enzyme that catalyzes conversion of A to B may be induced in the presence of A in the media. Expression of such pathway enzymes may be induced either by adding the compound that causes induction or by the natural build-up of the compound during the process of the biosynthetic pathway (e.g., the inducer may be an intermediate produced during the biosynthetic process to yield a desired product).

One of ordinary skill in the art should appreciate that the designation of the enzymes are governed by the specific reaction catalyzed by them as is depicted in FIG. 1. It is possible for a single enzyme to catalyze two reactions that are chemically identical but are assigned to different pathways on the basis of the respective substrate. This may be associated with different enzyme classification numbers (e.g. EC numbers). In some instance, enzymes have not been yet allocated an EC number, which is why reference is only made for definition of the relevant enzymatic reaction.

In some embodiments, computer-implemented design techniques may be used to generate alternative pathways for generating an organic compound of interest. In some embodiments, the databases contain genomic information and their link may be utilized for designing novel metabolic pathways. Examples of databases are MetaCyc (a database of metabolic pathways and enzymes), the University of Minnesota biocatalysis/biodegradation database (a database of microbial catalytic reactions and biodegradation pathways for organic chemical compounds), LGAND (a composite database that provides information about metabolites and other chemical compounds, substrate-product relations representing metabolic and other reactions and information about enzyme molecules) and KEGG (Kyoto Encyclopedia of Genes and Genomes). Specific polypeptide sequences that are relevant for the pathways described herein are available using the Uniport number as provided by the Universal Protein Resource database. A database of pathway components may also contain components of predicted, putative, or unknown functions. It may also contain pseudo-components of defined function that may have an undefined composition. In some embodiments, a program may design combinations of regulatory and/or functional elements that are in the public domain (e.g., that are not covered by patent rights and/or are not subject to a licensing fee). Databases of freely available genetic elements may be generated and/or used as a source of nucleic acid sequences that can be combined to produce alternative pathways. Alternative pathways containing different combinations of known functional and/or regulatory elements (e.g., from different species) may be designed, assembled, and/or tested. Libraries including variations in enzymatic element regions may be used to ascertain the relative effects of different types of enzymes or of different variants of the same enzyme. Libraries including variations in regulatory element regions may be used to ascertain the optimal expression level or regulatory control among a set of genes. In some embodiments, the functional properties of different engineered pathways may be tested in vivo by transforming host cells or organisms with the appropriate assembled nucleic acids, and assaying the properties of the engineered organisms. In some embodiments, the functional properties of different engineered pathways may be tested in vitro by isolating components expressed from assembled nucleic acids and testing the appropriate combinations of components in an in vitro system.

Aspects of the invention provide several metabolic pathways that can be used to produce organic compounds such as the products described herein. Moreover, the products can be converted in vitro through enzymatic or chemical reactions into additional molecules of interest. These pathways are shown in FIG. 1. Accordingly, aspects of the invention provide a recombinant microorganism having an engineered biosynthetic pathway shown in FIG. 1. These engineered microorganisms may be also genetically engineered to increase L-lysine production. Accordingly, in some embodiments, recombinant microorganisms have at least one gene for enhanced lysine production that is expressed at a level lower or higher than that expressed prior to manipulation of the microorganism or in a comparable microorganism which has not been manipulated. Genes are selected from the group of genes which play a key role in the biosynthesis of lysine such as aspartokinase, aspartate semialdehyde dehydrogenase, dihydrodipicolinate synthase, dihydrodipicolinate reductase, tetrahydrodipicolinate succinylase, succinyl-amino-ketopimelate transaminase, succinyl-diamino-pimelate desuccinylase, diaminopimelate epimerase, diaminopimelate dehydrogenase, arginyl-tRNA synthetase, diaminopimelate decarboxylase, pyruvate carboxylase, phosphoenolpyruvate carboxylase, glucose-6-phosphate dehydrogenase, transketolase, transaldolase, phosphogluconolactonase, fructose 1,6-biphosphatase, homoserine dehydrogenase, phophoenolpyruvate carboxykinase, succinyl-CoA synthetase, methyl-malonyl-CoA mutase. The up regulation of Lysine production through one or more of the genetic manipulations described above, can then be used in combination with an enzyme selected from anyone of Tables 1-13 to produce products.

As described in FIG. 1 (S)-2-amino 6-hydroxypimelate is an intermediate to several pathways that can be used to produce a variety of products. (S)-2-amino 6-hydroxypimelate can be made by reacting (S)-2-amino-6-oxopimelate with a 2-oxoacid reductase (step A, FIG. 1) with an enzyme such as an enzyme described in Table 1, below.

TABLE 1

Reaction A

| Enzyme | E.C. Number | Uniprot |
| --- | --- | --- |
| 2-oxo-acid/reductase reductase | 1.1.1.X | |
| 2-oxo-acid reductase | 1.1.99.X | |
| diacetyl reductase [(S)-acetoin forming] | 1.1.1.303 (formerly 1.1.1.5) | P39714 |
| diacetyl reductase [(S)-acetoin forming] | 1.1.1.304 (formerly 1.1.1.5) | Q48436 |
| glyoxylate reductase | 1.1.1.26 | O58320 |
| L-lactate dehydrogenase | 1.1.1.27 | Q81EP4 |
| malate dehydrogenase | 1.1.1.37 | P10584 |
| tartrate dehydrogenase | 1.1.1.93 | Q51945 |
| indolelactate dehydrogenase | 1.1.1.110 | E1S7U8 |
| 3-(imidazol-5-yl)lactate dehydrogenase | 1.1.1.111 | |
| 2-dehydropantoate 2-reductase | 1.1.1.169 | P0A9J4 |
| 2-oxoadipate reductase | 1.1.1.172 | |
| 2-hydroxyglutarate dehydrogenase | 1.1.99.2 | Q9H9P8 |
| gluconate 2-dehydrogenase (acceptor) | 1.1.99.3 | Q6B3Y5 |
| 2-oxo-acid reductase | 1.1.99.30 | |
| (R)-2-hydroxy-fatty-acid dehydrogenase | 1.1.1.98 | |
| D-2-hydroxyacid dehydrogenase | 1.1.1.345 | |
| (S)-2-hydroxy-acid oxidase | 1.1.3.15 | P05414 |

As described in FIG. 1, (S)-2-amino 6-hydroxypimelate can be used as a substrate for the formation of either (S)-2-amino-6-hydroxypimeloyl-CoA or (S)-2-amino-5-heptenedioate. (S)-2-amino-6-hydroxypimeloyl-CoA and (S)-2-amino-5-heptenedioate can be used as shown in FIG. 1, to form additional products. (S)-2-amino-6-hydroxypimeloyl-CoA is formed by reacting (S)-2-amino 6-hydroxypimelate with one or more enzymes selected from those provided in Table 2, below.

TABLE 2

Reaction B

| Enzyme | E.C. Number | Uniprot |
| --- | --- | --- |
| CoA transferases | 2.8.3.X | |
| CoA Ligase | 6.2.1.X | |
| glutaconate CoA transferase | 2.8.3.12 | E3PWJ4, E3PWJ5 |

(S)-2-amino-5-heptenedioate is formed by reacting (S)-2-amino 6-hydroxypimelate with one or more enzymes selected from those provided in Table 3, below.

TABLE 3

Reaction C

| Enzyme | E.C. Number | Uniprot |
|---|---|---|
| dehydratase | 4.2.1.X | |

(S)-2-amino-6-hydroxypimeloyl-CoA can be reacted with one or more enzymes selected from those shown in Table 4, below, to form (S)-1-amino-1-carboxy-2-hexenoyl-CoA.

TABLE 4

Reaction D

| Enzyme | E.C. Number | Uniprot |
|---|---|---|
| Dehydratase | 4.2.1.X | |
| 2-hydroxyglutaryl CoA dehydratase | 4.2.1.X | Ref* |
| lactoyl-CoA dehydratase | 4.2.1.54 | G3KIM3, G3KIM4 |
| Itaconyl-CoA hydratase | 4.2.1.56 | |

*Ref Substrate Specificity of 2-Hydroxyglutaryl-CoA Dehydratase from *Clostridium symbiosum*: Toward a Bio-Based Production of Adipic Acid, Anutthaman Parthasarathy, Antonio J. Pierik, Jörg Kahnt, Oskar Zelder, and Wolfgang Buckel *Biochemistry* 50 (17), 3540-3550, 2011.

(S)-2-amino-5-heptenedioate can be reacted with one or more enzymes selected from those shown in Table 5, below, to form alpha-aminopimelate.

TABLE 5

Reaction E

| Enzyme | E.C. Number | Uniprot |
|---|---|---|
| enoate reductase | 1.3.1.X | |
| fumarate reductase | 1.3.1.6 | P32614 |
| 2-enoate reductase | 1.3.1.31 | P40952 |
| maleylacetate reductase | 1.3.1.32 | Q8NL91 |

(S)-1-amino-1-carboxy-2-hexenoyl-CoA can be reacted with one or more enzymes selected from those shown in Table 6, below to form (S)-2-aminopimeloyl-CoA.

TABLE 6

Reaction F

| Enzyme | E.C. Number | Uniprot |
|---|---|---|
| acrylyl-CoA reductase | 1.3.1.X | |
| acyl-CoA dehydrogenase | 1.3.8.X | |
| acrylyl-CoA reductase | 1.3.1.B1 | |
| acyl-CoA dehydrogenase | 1.3.1.8 | Q3IAA0 |
| enoyl-[acyl-carrier-protein] reductase | 1.3.1.9 | P54616 |
| enoyl-[acyl-carrier-protein] reductase (NADPH, B-specific) | 1.3.1.10 | Q8WZM3 |
| cis-2-enoyl-CoA reductase | 1.3.1.37 | |
| trans-2-enoyl-CoA reductase | 1.3.1.38 | Q9BY49 |
| 2-hydroxy-6-oxo-6-phenylhexa-2,4-dienoate reductase | 1.3.1.39 | |
| 2'-hydroxyisoflavone reductase | 1.3.1.45 | P52575 |

TABLE 6-continued

Reaction F

| Enzyme | E.C. Number | Uniprot |
|---|---|---|
| pimeloyl-CoA dehydrogenase | 1.3.1.62 | D3RZ02, D3RZ15, Q0K4A3, Q0K4A2 |
| short-chain acyl-CoA dehydrogenase | 1.3.8.1 | Q06319 |
| medium-chain acyl-CoA dehydrogenase | 1.3.8.7 | P08503 | alpha-aminopimelate can be reacted with one or more enzyme selected from those in Table 7, below, to form 2-amino-7-oxoheptanoate.

TABLE 7

Reaction G and G¹

| Enzyme | E.C. Number | Uniprot |
|---|---|---|
| aldehyde dehydrogenase | 1.2.1.X | |
| aldehyde dehydrogenase (NAD+) | 1.2.1.3 | Q4F895 |
| aldehyde dehydrogenase (NADP+) | 1.2.1.4 | E4R8S4 |
| aldehyde dehydrogenase [NAD(P)+] | 1.2.1.5 | P11884 |
| gamma-glutamyl-gamma-aminobutyraldehyde dehydrogenase (NAD+) | 1.2.1.B6 | A6T782 |
| benzaldehyde dehydrogenase (NADP+) | 1.2.1.7 | |
| aminobutyraldehyde dehydrogenase | 1.2.1.19 | P77674 |
| glutarate-semialdehyde dehydrogenase | 1.2.1.20 | |
| benzaldehyde dehydrogenase (NAD+) | 1.2.1.28 | M1YF02 |
| L-aminoadipate-semialdehyde dehydrogenase | 1.2.1.31 | P07702 |
| 6-oxohexanoate dehydrogenase | 1.2.1.63 | Q0RWL6 |

(S)-2-aminopimeloyl-CoA can be reacted with one or more enzymes selected from those shown in Table 8, below, to form 2-amino-7-oxoheptanoate.

TABLE 8

Reaction H

| Enzyme | E.C. Number | Uniprot |
|---|---|---|
| dehydrogenase (acylating) | 1.2.1.X | |
| glyoxylate dehydrogenase (acylating) | 1.2.1.17 | |
| cinnamoyl-CoA reductase | 1.2.1.44 | Q9S9N9 |
| hexadecanal dehydrogenase (acylating) | 1.2.1.42 | Q39152 |
| long-chain-fatty-acyl-CoA reductase | 1.2.1.50 | Q8RR58 |
| malonyl CoA reductase (malonate semialdehyde-forming | 1.2.1.75 | Q96YK1 |
| succinate-semialdehyde dehydrogenase (acylating) | 1.2.1.76 | A4YEN2 |

(S)-2-amino-5-heptenedioate and alpha-aminopimelate can be reacted with one or more enzymes selected from those shown in Table 9, below, to make (S)-1-amino-1-carboxy-2-hexenoyl-CoA or (S)-2-aminopimeloyl-CoA, respectively. One of ordinary skill in the art will appreciate that the choice of which enzyme to use in the desired pathway will result in a selectivity for the substrate and, therefore, control the outcome of the desired pathway.

TABLE 9

Reactions I and J

| Enzyme | E.C. Number | Uniprot |
|---|---|---|
| CoA transferases | 2.8.3.X | |
| CoA ligase | 6.2.1.X | |
| propionate CoA-transferase | 2.8.3.1 | Q9L3F7 |
| glutaconate CoA transferase | 2.8.3.12 | Q59111, Q59112 |
| 5-hydroxypentanoate CoA-transferase | 2.8.3.14 | |
| O-succinylbenzoate-CoA ligase (ADP-forming) | 6.2.1.B1 | |
| butyrate-CoA ligase | 6.2.1.2 | Q9C8D4 |
| Glutarate-CoA ligase | 6.2.1.6 | A9WLI0 |
| 4-Coumarate-CoA ligase | 6.2.1.12 | Q9S725, Q42524 |
| 6-Carboxyhexanoate-CoA ligase | 6.2.1.14 | Q9ZER2 |
| dicarboxylate-CoA ligase | 6.2.1.23 | |
| Benzoate-CoA ligase | 6.2.1.25 | Q13WK3 |

(S)-1-amino-1-carboxy-2-hexenoyl-CoA and (S)-2-aminopimeloyl-CoA can be reacted with one or more enzymes selected from those shown in Table 10, below, to form (S)-2-amino-5-heptenedioate and alpha-aminopimelate, respectively. One of ordinary skill in the art will appreciate that the choice of which enzyme to use in the desired pathway will result in a selectivity for the substrate and, therefore, control the outcome of the desired pathway.

TABLE 10

Reactions I¹ or J¹

| Enzyme | E.C. Number | Uniprot |
|---|---|---|
| CoA transferases | 2.8.3.X | |
| thioesterase/hydrolase | 3.1.2.X | |
| propionate CoA-transferase | 2.8.3.1 | Q9L3F7 |
| glutaconate CoA transferase | 2.8.3.12 | Q59111 |
| 5-hydroxypentanoate CoA-transferase | 2.8.3.14 | |
| succinyl-CoA hydrolase | 3.1.2.3 | Ref* |
| 3-hydroxyisobutyryl-CoA hydrolase | 3.1.2.4 | Q6NVY1 |
| acyl-CoA hydrolase | 3.1.2.20 | P44886 |
| 4-hydroxybenzoyl-CoA thioesterase | 3.1.2.23 | P56653 |

Ref* Westin M A, Hunt M C, Alexson S E. The identification of a succinyl-CoA thioesterase suggests a novel pathway for succinate production in peroxisomes. *J Biol Chem.* Nov 18; 280(46): 38125-32, 2005.

Alpha-aminopimelate can be reacted with one or more of the enzymes shown in Table 11, below, to form amino caproic acid. The enzyme selected for this reaction will have a preference for alpha-aminopimelate over other potential substrates. For example, given the potential substrates available to the enzyme, the enzyme will be more likely to react with alpha-aminopimelate than other locally available substrates.

TABLE 11

Reaction K

| Enzyme | E.C. Number | Uniprot |
|---|---|---|
| amino acid decarboxylase | 4.1.1.X | |
| benzoylformate decarboxylase | 4.1.1.7 | P20906 |
| aspartate 1-decarboxylase | 4.1.1.11 | P0A790 |
| glutamate decarboxylase | 4.1.1.15 | P69910 |
| ornithine decarboxylase | 4.1.1.17 | P43099 |

TABLE 11-continued

Reaction K

| Enzyme | E.C. Number | Uniprot |
|---|---|---|
| lysine decarboxylase | 4.1.1.18 | P0A9H3 |
| arginine decarboxylase | 4.1.1.19 | Q7MK24 |
| diaminopimelate decarboxylase | 4.1.1.20 | P00861 |
| Tyrosine decarboxylase | 4.1.1.25 | Q60358 |
| aromatic-L-amino-acid decarboxylase | 4.1.1.28 | P80041 |
| diaminobutyrate decarboxylase | 4.1.1.86 | P56744 |

2-amino-7-oxoheptanoate can be reacted with one or more enzymes selected from those shown in Table 12, below, to form homolysine.

TABLE 12

Reaction L

| Enzyme | E.C. Number | Uniprot |
|---|---|---|
| amine dehydrogenase | 1.4.1.X | |
| transaminase | 2.6.1.X | |
| 4-aminobutyrate-2-oxoglutarate transaminase | 2.6.1.13 | P38021 |
| lysine 6-dehydrogenase | 1.4.1.18 | O59312 |
| 4-aminobutyrate-2-oxoglutarate transaminase | 2.6.1.19 | 4KKA1 |
| (S)-3-amino-2-methylpropionate transaminase | 2.6.1.22 | P80147 |
| L-lysine 6-transaminase | 2.6.1.36 | Q5XPV2 |
| lysine-pyruvate 6-transaminase | 2.6.1.71 | Ref* |
| diaminobutyrate-2-oxoglutarate transaminase | 2.6.1.76 | P56744 |
| 4-aminobutyrate-pyruvate transaminase | 2.6.1.96 | Q94CE5 |

Ref* A novel enzyme, L-lysine: pyruvate aminotransferase, catalyses the first step of lysine catabolism in *Pichia guilliermondii*, Schmidt, H.; Bode, R.; Birnbaum, D.; *FEMS Microbiol. Lett.* 49, 203-206 (1988).

Homolysine can be reacted with one or more enzymes selected from those shown in Table 13, below, to form HMDA. The enzyme selected for this reaction will have a preference for homolysine over other potential substrates. For example, given the potential substrates available to the enzyme, the enzyme will be more likely to react with homolysine than other locally available substrates.

TABLE 13

Reaction M

| Enzyme | E.C. Number | Uniprot |
|---|---|---|
| amino acid decarboxylase | 4.1.1.X | |
| benzoylformate decarboxylase | 4.1.1.7 | P20906 |
| aspartate 1-decarboxylase | 4.1.1.11 | P0A790 |
| glutamate decarboxylase | 4.1.1.15 | Q9AR41 |
| ornithine decarboxylase | 4.1.1.17 | P21169 |
| arginine decarboxylase | 4.1.1.18 | P0A9H3, P52095 |
| diaminopimelate decarboxylase | 4.1.1.20 | P00861 |
| Tyrosine decarboxylase | 4.1.1.25 | Q60358 |
| aromatic-L-amino-acid decarboxylase | 4.1.1.28 | P14173 |
| Indolepyruvate decarboxylase | 4.1.1.74 | Q63B94 |
| diaminobutyrate decarboxylase | 4.1.1.86 | P56744 |

One of ordinary skill in the art will appreciate that FIG. 1 shows a variety of different pathways that can be used to form end products such as ACA and HMDA. Accordingly, a variety of recombinant microorganisms are described which are engineered to include one or more enzymes show in FIG. 1 and the accompanying tables, in combination with a recombinant sequence to up regulate lysine production. Other recombinant microorganisms include recombinant sequences that allow for the increased production of two, three, four or more enzymes described in FIG. 1 and the accompanying text. The following exemplary microorganisms can be used to produce intermediates, ACA and/or HMDA.

A microorganism for the production of ACA can be engineered to express at least one, two, three, or four enzymes selected from those shown in Tables 1, 3, 5, and 11. Another microorganism for the production of ACA can be engineered to express at least one, two, three, or four enzymes selected from those shown in Tables 1, 2, 4, 5, 9 and 11. In another example, a microorganism for the production of ACA can be engineered to express at least one, two, or three enzymes selected from those shown in Tables 1, 2, 4, 6, 10 and 11. In yet another example, a microorganism for the production of ACA can be engineered to express at least one, two, or three enzymes selected from those shown in Tables 1, 3, 9, 6, 10, and 11. One of ordinary skill in the art will appreciate that with reference to FIG. 1 and the accompanying tables, additional recombinant microorganisms can be created to produce ACA.

Similarly, a microorganism for the production of HMDA can be engineered to express at least one, two, three, or four enzymes selected from those shown in Tables 1, 3, 5, 7, 12 and 13. Another microorganism for the production of HMDA can be engineered to express at least one, two, three, or four enzymes selected from those shown in Tables 1, 3, 9, 6, 8, 12, and 13. In another example, a microorganism for the production of HMDA can be engineered to express at least one, two, or three enzymes selected from those shown in Tables 1, 2, 4, 6, 8, 12 and 13. In yet another example, a microorganism for the production of ACA can be engineered to express at least one, two, or three enzymes selected from those shown in Tables 1, 2, 4, 10, 5, 7, 12 and 13. Additional examples of pathways that can be used to produce HMDA include combinations of enzymes shown in Tables 1, 2, 4, 10, 5, 7, 12, 13; 1, 2, 4, 10, 5, 9, 8, 12, 13; and 1, 2, 4, 6, 10, 7, 12, 13. One of ordinary skill in the art will appreciate that with reference to FIG. 1 and the accompanying tables, additional recombinant microorganisms can be created to produce HMDA.

B. Making Products

The recombinant microorganisms described herein may be cultivated continuously or discontinuously in a batch process (batch cultivation) or in a fed-batch process (feed process) or repeated fed-batch process (repetitive feed process) for the purposes of producing products.

The culture medium to be used must satisfy in a suitable manner the requirements of the respective strains. Descriptions of culture media for various microorganisms are contained in the handbook "Manual of Methods for General Bacteriology" of the American Society for Bacteriology (Washington D.C., USA, 1981). Media must contain suitable carbon sources such as monosaccharides (e.g. glucose and fructose), oligosaccharides (e.g. sucrose, lactose), polysaccharides (e.g. starch and cellulose), oils and fats or mixture thereof. Media must contain a nitrogen source such as organic nitrogen-containing compounds such as peptones, yeast extract, meat extract, malt extract, corn steep liquor, soy bean flour and urea, or inorganic compounds such as ammonium sulfate, ammonium chloride, ammonium phosphate, ammonium carbonate and ammonium nitrate. The nitrogen sources may be used individually or as a mixture.

In addition to the carbon sources and nitrogen sources, media must contain suitable minerals, salts, cofactors, buffers and other components, known to those skilled in the art, suitable for growth of the culture and promotion of product production.

Typically cells are grown at a temperature in the range of 20° C. to about 45° C. and preferably 25° C. to 40° C. in an appropriate medium. Suitable growth media includes common commercially available media such as Luria Bertani (LB) broth, Yeast medium (YM) or any synthetic or defined media. Suitable pH ranges are between pH 5.0 to pH 9.0. In order to regulate the pH of the culture, basic compounds such as sodium hydroxide, potassium hydroxide, ammonia or ammonia water, or acidic compounds such as phosphoric acid or sulfuric acid are used as appropriate. Culture may be performed under aerobic or anaerobic conditions.

In accordance with the methods described herein, reaction mixtures for pathway development may be carried out in any vessel that permits cell growth and/or incubation. For example, a reaction mixture may be a bioreactor, a cell culture flask or plate, a multiwell plate (e.g., a 96, 384, 1056 well microtiter plates, etc.), a culture flask, a fermentor, or other vessel for cell growth or incubation.

Screening for the expression of a particular recombinant sequence can be accomplished using any technique known in the art. For example, screening may be carried out by detection of expression of a selectable marker, which, in some genetic circumstances, allows cells expressing the marker to survive while other cells die (or vice versa). Efficient screening techniques are needed to provide efficient development of novel pathways using the methods described herein. Preferably, suitable screening techniques for compounds produced by the enzymatic pathways allow for a rapid and sensitive screen for the properties of interest. Visual (colorimetric) assays are optimal in this regard, and are easily applied for compounds with suitable light absorption properties. More sophisticated screening technologies include, for instance, high-throughput HPLC-MS analysis, SPME (Solid Phase Microextraction) and GC-MS (Gas chromatography-mass spectrometry) (see Handbook of analytical derivatization reaction, D. R. Knapp; John Wiley & Sons, 1979). In some instance, screening robots are connected to HPLC-MS systems for automated injection and rapid sample analysis. These techniques allow for high-throughput detection and quantification of virtually any desired compound.

Produced products of interest may be isolated from the fermentation medium or cell extract using methods known in the art. For example, solids or cell debris may be removed by centrifugation, filtration, decantation and the like. Products may be isolated by distillation, liquid-liquid extraction, membrane evaporation, adsorption, or using any methods known in the art.

In some embodiments, identification of the product of interest may be performed using an HPLC. For example, the standard samples are prepared with known amounts of the organic product in the medium (e.g. HMDA and ACA). The retention time of the adipic acid produced can then be compared to that of the authentic standard. In some embodiments, identification of the product of interest may be performed using a GC-MS. The resolved samples are then analyzed by a mass selective detector and compared to previous mass spectra and retention time of authentic standards.

The practice of the present methods will employ, unless otherwise indicated, conventional techniques of cell biology, cell culture, molecular biology, transgenic biology, microbiology, recombinant DNA, and immunology, engineering, robotics, optics, computer software and integration. The techniques and procedures are generally performed according to conventional methods in the art and various general references. Such techniques are explained fully in the literature. See, for example, Molecular Cloning A Laboratory Manual, 2nd Ed., ed. by Sambrook, Fritsch and Maniatis (Cold Spring Harbor Laboratory Press: 1989); DNA Cloning, Volumes I and II (D. N. Glover ed., 1985); Oligonucleotide Synthesis (M. J. Gait ed., 1984); Mullis et al. U.S. Pat. No. 4,683,195; Nucleic Acid Hybridization (B. D. Hames & S. J. Higgins eds. 1984); Transcription And Translation (B. D. Hames & S. J. Higgins eds. 1984); Culture Of Animal Cells (R. I. Freshney, Alan R. Liss, Inc., 1987); Immobilized Cells And Enzymes (IRL Press, 1986); B. Perbal, A Practical Guide To Molecular Cloning (1984); the treatise, Methods In Enzymology (Academic Press, Inc., N.Y.); Gene Transfer Vectors For Mammalian Cells (J. H. Miller and M. P. Calos eds., 1987, Cold Spring Harbor Laboratory); Methods In Enzymology, Vols. 154 and 155 (Wu et al. eds.), Immunochemical Methods In Cell And Molecular Biology (Mayer and Walker, eds., Academic Press, London, 1987); Handbook Of Experimental Immunology, Volumes I-IV (D. M. Weir and C. C. Blackwell, eds., 1986); Manipulating the Mouse Embryo, (Cold Spring Harbor Laboratory Press, Cold Spring Harbor, N.Y., 1986); Lakowicz, J. R. Principles of Fluorescence Spectroscopy, New York: Plenum Press (1983), and Lakowicz, J. R. Emerging Applications of Fluorescence Spectroscopy to Cellular Imaging: Lifetime Imaging, Metal-ligand Probes, Multi-photon Excitation and Light Quenching, Scanning Microsc. Suppl. VOL. 10 (1996) pages 213-24, for fluorescent techniques, Optics Guide 5 Melles Griot® Irvine Calif. for general optical methods, Optical Waveguide Theory, Snyder & Love, published by Chapman & Hall, and Fiber Optics Devices and Systems by Peter Cheo, published by Prentice-Hall for fiber optic theory and materials.

EXAMPLES

The following reference materials are used in the following Examples: Recombinant DNA manipulations generally follow methods described by Sambrook et al. Molecular Cloning: A Laboratory Manual, Third Edition, Sambrook and Russell, 2001, Cold Spring Harbor Laboratory Press, 3rd Edition. Restriction enzymes are purchased from New England Biolabs (NEB). T4 DNA ligase is obtained from Invitrogen. FAST-LINK™ DNA Ligation Kit is obtained from Epicentre. Zymoclean Gel DNA Recovery Kit and DNA Clean & Concentrator Kit are obtained from Zymo Research Company. Maxi and Midi Plasmid Purification Kits are obtained from Qiagen. Antarctic phosphatase is obtained from NEB. Agarose (electrophoresis grade) is obtained from Invitrogen. TE buffer contains 10 mM Tris-HCl (pH 8.0) and 1 mM Na2EDTA (pH 8.0). TAE buffer contains 40 mM Tris-acetate (pH 8.0) and 2 mM Na2EDTA.

In Examples 1, restriction enzyme digests are performed in buffers provided by NEB. A typical restriction enzyme digest contains 0.8 μg of DNA in 8 μL of TE, 2 μL of restriction enzyme buffer (10× concentration), 1 μL of bovine serum albumin (0.1 mg/mL), 1 μL of restriction enzyme and 8 μL TE. Reactions are incubated at 37° C. for 1 h and analyzed by agarose gel electrophoresis. When DNA is required for cloning experiments, the digest is terminated by heating at 70° C. for 15 min followed by extraction of the DNA using Zymoclean gel DNA recovery kit.

The concentration of DNA in the sample is determined as follows. An aliquot (10 μL) of DNA is diluted to 1 mL in TE and the absorbance at 260 nm is measured relative to the absorbance of TE. The DNA concentration is calculated based on the fact that the absorbance at 260 nm of 50 μg/mL of double stranded DNA is 1.0.

Agarose gel typically contains 0.7% agarose (w/v) in TAE buffer. Ethidium bromide (0.5 μg/ml) is added to the agarose to allow visualization of DNA fragments under a UV lamp. Agarose gel is run in TAE buffer. The size of the DNA fragments is determined using two sets of 1 kb Plus DNA Ladder obtained from Invitrogen.

Example 1

Cloning of a plasmid expressing enzymatic pathway to hexamethylenediamine. The DNA fragments encoding 2-oxo-acid reductase (Step A in FIG. 1), CoA transferase (Step B in FIG. 1), dehydratase (Step D in FIG. 1), acyl-CoA dehydrogenase (Step F in FIG. 1), dehydrogenase (Step H in FIG. 1), amine dehydrogenase (Step L in FIG. 1) and homolysine decarboxylase (Step M in FIG. 1) are cloned into an expression vector. Gene candidates and their sequence are shown in Tables 1, 2, 4, 6, 8, 12 and 13. The resulting plasmid that successfully transcribes all pathway genes is designated pBA901.

Example 2

Circular plasmid DNA molecules are introduced into target *E. coli* cells by chemical transformation or electroporation. For chemical transformation, cells are grown to mid-log growth phase, as determined by the optical density at 600 nm (0.5-0.8). The cells are harvested, washed and finally treated with CaCl2. To chemically transform these *E. coli* cells, purified plasmid DNA is allowed to mix with the cell suspension in a microcentrifuge tube on ice. A heat shock is applied to the mixture and followed by a 30-60 min recovery incubation in rich culture medium. For electroporation, *E. coli* cells grown to mid-log growth phase are washed with water several times and finally resuspended into 10% glycerol solution. To electroporate DNA into these cells, a mixture of cells and DNA is pipetted into a disposable plastic cuvette containing electrodes. A short electric pulse is then applied to the cells which to form small holes in the membrane where DNA can enter. The cell suspension is then incubated with rich liquid medium followed by plating on solid agar plates. Detailed protocol can be obtained in Molecular Cloning: A Laboratory Manual, Third Edition, Sambrook and Russell, 2001, Cold Spring Harbor Laboratory Press, 3rd Edition.

*E. coli* cells of the BL21 strain are transformed with plasmid pBA901. BL21 is a strain of *E. coli* having the genotype: B F-dcm ompT hsdS(rB-mB-) gal λ. BL21 transformant of pBA901 is also called biocatalyst BA901.

Example 3

Cell Lysis Method. *E. coli* cell culture is spun down by centrifugation at 4000 rpm. The cell-free supernatant is discarded and the cell pellet is collected. After being collected and resuspended in the proper resuspension buffer (50 mM phosphate buffer at pH 7.5), the cells are disrupted by chemical lysis using BUGBUSTER® reagent (Novagen). Cellular debris is removed from the lysate by centrifugation (48,000 g, 20 min, 4° C.). Protein is quantified using the Bradford dye-binding procedure. A standard curve is prepared using bovine serum albumin. Protein assay solution is purchased from Bio-Rad and used as described by the manufacturer.

Growth Medium. For the following Examples, Examples 5-6, the Growth Medium is prepared as follows:

All solutions are prepared in distilled, deionized water. LB medium (1 L) contained Bacto tryptone (i.e. enzymatic digest of casein) (10 g), Bacto yeast extract (i.e. water soluble portion of autolyzed yeast cell) (5 g), and NaCl (10 g). LB-glucose medium contained glucose (10 g), MgSO4 (0.12 g), and thiamine hydrochloride (0.001 g) in 1 L of LB medium. LB-freeze buffer contains K2HPO4 (6.3 g), KH2PO4 (1.8 g), MgSO4 (1.0 g), (NH4)2SO4 (0.9 g), sodium citrate dihydrate (0.5 g) and glycerol (44 mL) in 1 L of LB medium. M9 salts (1 L) contains Na2HPO4 (6 g), K(H2PO4 (3 g), NH4Cl (1 g), and NaCl (0.5 g). M9 minimal medium contains D-glucose (10 g), MgSO4 (0.12 g), and thiamine hydrochloride (0.001 g) in 1 L of M9 salts. Antibiotics are added where appropriate to the following final concentrations: ampicillin (Ap), 50 µg/mL; chloramphenicol (Cm), 20 µg/mL; kanamycin (Kan), 50 µg/mL; tetracycline (Tc), 12.51 µg/mL. Stock solutions of antibiotics are prepared in water with the exceptions of chloramphenicol which is prepared in 95% ethanol and tetracycline which is prepared in 50% aqueous ethanol. Aqueous stock solutions of isopropyl-β-D-thiogalactopyranoside (IPTG) are prepared at various concentrations.

The standard fermentation medium (1 L) contains K2HPO4 (7.5 g), ammonium iron (III) citrate (0.3 g), citric acid monohydrate (2.1 g), and concentrated H2SO4 (1.2 mL). Fermentation medium is adjusted to pH 7.0 by addition of concentrated NH4OH before autoclaving. The following supplements are added immediately prior to initiation of the fermentation: D-glucose, MgSO4 (0.24 g), potassium and trace minerals including (NH4)6(Mo7O24).4H2O (0.0037 g), ZnSO4.7H2O (0.0029 g), H3BO3 (0.0247 g), CuSO4.5H2O (0.0025 g), and MnCl2.4H2O (0.0158 g). IPTG stock solution is added as necessary (e.g., when optical density at 600 nm lies between 15-20) to the indicated final concentration. Glucose feed solution and MgSO4 (1 M) solution are autoclaved separately. Glucose feed solution (650 g/L) is prepared by combining 300 g of glucose and 280 mL of H2O. Solutions of trace minerals and IPTG are sterilized through 0.22-µm membranes. Antifoam (Sigma 204) is added to the fermentation broth as needed.

Example 4

Shake Flask Experiments for Hexamethylenediamine Production. Seed inoculant is started by introducing a single colony of biocatalyst BA901 picked from a LB agar plate into 50 mL TB medium (1.2% w/v Bacto Tryptone, 2.4% w/v Bacto Yeast Extract, 0.4% v/v glycerol, 0.017 M KH2PO4, 0.072 M K2HPO4). Culture is grown overnight at 37° C. with agitation at 250 rpm until they are turbid. A 2.5 mL aliquot of this culture is subsequently transferred to 50 mL of fresh TB medium. After culturing at 37° C. and 250 rpm for an additional 3 h, IPTG is added to a final concentration of 0.2 mM. The resulting culture is allowed to grow at 27° C. for 4 hours. Cells are harvested, washed twice with PBS medium, and resuspended in 0.5 original volume of M9 medium supplemented with glucose (2 g/L). The whole cell suspension is then incubated at 27° C. for 48 h. Samples is taken and analyzed by GC/MS and 1H-NMR. Compared to the control BL21 strain transformed with empty plasmids that no hexamethylenediamine production is detected, *E. coli* BA901 produces hexamethylenediamine at a concentration above 0.5 g/L in shake flasks from glucose.

Example 5

Cultivation of Hexamethylenediamine Biocatalyst Under Fermentor-Controlled Conditions. Fed-batch fermentation is performed in a 2 L working capacity fermentor. Temperature, pH and dissolved oxygen are controlled by PID control loops. Temperature is maintained at 37° C. by temperature adjusted water flow through a jacket surrounding the fermentor vessel at the growth phase, and later adjusted to 27° C. when production phase starts. The pH is maintained at 7.0 by the addition of 5 N KOH and 3 N H3PO4. Dissolved oxygen (DO) level is maintained at 20% of air saturation by adjusting air feed as well as agitation speed.

Inoculant is started by introducing a single colony of BA901 picked from an LB agar plate into 50 mL TB medium. The culture is grown at 37° C. with agitation at 250 rpm until the medium is turbid. Subsequently a 100 mL seed culture is transferred to fresh M9 glucose medium. After culturing at 37° C. and 250 rpm for an additional 10 h, an aliquot (50 mL) of the inoculant (OD600=6-8) is transferred into the fermentation vessel and the batch fermentation is initiated. The initial glucose concentration in the fermentation medium is about 40 g/L.

Cultivation under fermentor-controlled conditions is divided into two stages. In the first stage, the airflow is kept at 300 ccm and the impeller speed is increased from 100 to 1000 rpm to maintain the DO at 20%. Once the impeller speed reaches its preset maximum at 1000 rpm, the mass flow controller starts to maintain the DO by oxygen supplementation from 0 to 100% of pure O2.

The initial batch of glucose is depleted in about 12 hours and glucose feed (650 g/L) is started to maintain glucose concentration in the vessel at 5-20 g/L. At OD600=20-25, IPTG stock solution is added to the culture medium to a final concentration of 0.2 mM. The temperature setting is decreased from 37 to 27° C. and the production stage (i.e., second stage) is initiated. Production stage fermentation is run for 48 hours and samples are removed to determine the cell density and quantify metabolites.

The hexamethylenediamine production is measured by GS/MS and 1H-NMR. Compared to the control BL21 strain transformed with empty plasmids, *E. coli* BA091 produced hexamethylenediamine from glucose at a concentration of above 0.5 µg/L under fermentor-controlled conditions.

Example 6

Cloning of a plasmid expressing enzymatic pathway to aminocaproic acid. DNA fragments encoding 2-oxo-acid reductase (Step A in FIG. 1), CoA transferase (Step B in FIG. 1), dehydratase (Step D in FIG. 1), CoA transferase (Step I in FIG. 1), enoate reductase (Step 5 in FIG. 1), and amino-acid decarboxylase (Step K in FIG. 1) are cloned into an expression vector. Gene candidates and their sequence are shown in Tables 1, 2, 4, 5, 9, and 11. The resulting plasmid that successfully transcribes all pathway genes is designated pBA902. The plasmid is then cloned and used to product ACA as described in Examples 2-5.

The invention claimed is:
1. A recombinant bacterial cell producing (S)-2-amino-6-hydroxypimelate, wherein the recombinant bacterial cell is genetically modified to produce (S)-2-amino-6-oxopimelate from diversion of the lysine biosynthesis pathway, wherein the recombinant bacterial cell comprises an exogenous nucleic acid encoding an enzyme that catalyzes a substrate to produce conversion of:
(A) (S)-2-amino-6-oxopimelate to (S)-2-amino-6-hydroxypimelate, wherein the enzyme that catalyzes reaction (A) is a diacetyl reductase [(S)-acetoin forming] belonging to E.C. 1.1.1.303, a diacetyl reductase [(S)-acetoin forming] belonging to E.C. 1.1.1.304, a glyoxylate reductase belonging to E.C. 1.1.1.26, an L-lactate dehydrogenase belonging to E.C. 1.1.1.27, a malate dehydrogenase belonging to E.C. 1.1.1.37, a tartrate dehydrogenase belonging to E.C. 1.1.1.93, an indole-lactate dehydrogenase belonging to E.C. 1.1.1.110, a 3-(imidazol-5-yl)lactate dehydrogenase belonging to E.C. 1.1.1.111, a 2-dehydropantoate 2-reductase belonging to E.C. 1.1.1.169, a 2-oxoadipate reductase belonging to E.C. 1.1.1.172, a 2-hydroxyglutarate dehydrogenase belonging to E.C. 1.1.99.2, a gluconate 2-dehydrogenase (acceptor) belonging to E.C. 1.1.99.3, a 2-oxo-acid reductase belonging to E.C. 1.1.99.30, an (R)-2-hydroxy-fatty-acid dehydrogenase belonging to E.C. 1.1.1.98, a D-2-hydroxyacid dehydrogenase belonging to E.C. 1.1.1.345, or an (S)-2-hydroxy-acid oxidase belonging to E.C. 1.1.3.15.

2. The recombinant bacterial cell of claim 1, wherein the recombinant bacterial cell further comprises at least one exogenous nucleic acid encoding at least one enzyme that catalyzes a substrate to product conversion that is:
(B) (S)-2-amino-6-hydroxypimelate to (S)-2-amino 6-hydroxypimeloyl-CoA, wherein the enzyme that catalyzes reaction (B) is a CoA ligase belonging to E.C. 6.2.1.X, or a glutaconate CoA transferase belonging to E.C. 2.8.3.12;
(D) (S)-2-amino 6-hydroxypimeloyl-CoA to (S)-1-amino-1-carboxy-2-hexenoyl-CoA wherein the enzyme that catalyzes reaction (D) is a 2-hydroxyglutaryl CoA dehydratase belonging to E.C. 4.2.1.X, a lactoyl-CoA dehydratase belonging to E.C. 4.2.1.54, or an itaconyl-CoA hydratase belonging to E.C. 4.2.1.56;
(F) (S)-1-amino-1-carboxy-2-hexenoyl-CoA to (S)-2-aminopimeloyl-CoA, wherein the enzyme that catalyzes reaction (F) is an acrylyl-CoA reductase belonging to E.C. 1.3.1.B1, an acyl-CoA dehydrogenase belonging to E.C. 1.3.1.8, an enoyl-[acyl-carrier-protein] reductase belonging to E.C. 1.3.1.9, an enoyl-[acyl-carrier-protein] reductase belonging to E.C. 1.3.1.10, a cis-2-enoyl-CoA reductase belonging to E.C. 1.3.1.37, a trans-2-enoyl-CoA reductase belonging to E.C. 1.3.1.38, a 2-hydroxy-6-oxo-6-phenylhexa-2,4-dienoate reductase belonging to E.C. 1.3.1.39, a 2'-hydroxyisoflavone reductase belonging to E.C. 1.3.1.45, a pimeloyl-CoA dehydrogenase belonging to E.C. 1.3.1.62, a short-chain acyl-CoA dehydrogenase belonging to E.C. 1.3.8.1, or a medium-chain acyl-CoA dehydrogenase belonging to E.C. 1.3.8.7;
(H) (S)-2-aminopimeloyl-CoA to 2-amino-7-oxoheptanoate, wherein the enzyme that catalyzes reaction (H) is a glyoxylate dehydrogenase (acylating) belonging to E.C. 1.2.1.17, a cinnamoyl-CoA reductase belonging to E.C. 1.2.1.44, a hexadecanal dehydrogenase (acylating) belonging to E.C. 1.2.1.42, a long-chain-fatty-acyl-CoA reductase belonging to E.C. 1.2.1.50, a malonyl CoA reductase (malonate semialdehyde-forming) belonging to E.C. 1.2.1.75, or a succinate-semialdehyde dehydrogenase (acylating) belonging to E.C. 1.2.1.76;
(L) 2-amino-7-oxoheptanoate to homolysine, wherein the enzyme that catalyzes reaction (L) is a 4-aminobutyrate-2-oxoglutarate transaminase belonging to E.C. 2.6.1.13, a lysine 6-dehydrogenase belonging to E.C. 1.4.1.18, a 4-aminobutyrate-2-oxoglutarate transaminase belonging to E.C. 2.6.1.19, an (S)-3-amino-2-methylpropionate transaminase belonging to E.C. 2.6.1.22, an L-lysine 6-transaminase belonging to E.C. 2.6.1.36, a lysine-pyruvate 6-transaminase belonging to E.C. 2.6.1.71, a diaminobutyrate-2-oxoglutarate transaminase belonging to E.C. 2.6.1.76, or a 4-aminobutyrate-pyruvate transaminase belonging to E.C. 2.6.1.96;
(M) homolysine to hexamethylenediamine, wherein the enzyme that catalyzes reaction (M) is a benzoylformate decarboxylase belonging to E.C. 4.1.1.7, an aspartate 1-decarboxylase belonging to E.C. 4.1.1.11, a glutamate decarboxylase belonging to E.C. 4.1.1.15, an ornithine decarboxylase belonging to E.C. 4.1.1.17, an arginine decarboxylase belonging to E.C. 4.1.1.18, a diaminopimelate decarboxylase belonging to E.C. 4.1.1.20, a tyrosine decarboxylase belonging to E.C. 4.1.1.25, an aromatic-L-amino-acid decarboxylase belonging to E.C. 4.1.1.28, an indolepyruvate decarboxylase belonging to E.C. 4.1.1.74, or a diaminobutyrate decarboxylase belonging to E.C. 4.1.1.86;
(J) (J1) (S)-2-aminopimeloyl-CoA to alpha-aminopimelate, or (J2) alpha-aminopimelate to (S)-2-aminopimeloyl-CoA, wherein:
the enzyme that catalyzes reaction (J1) is a propionate CoA-transferase belonging to E.C. 2.8.3.1, a glutaconate CoA transferase belonging to E.C. 2.8.3.12, a 5-hydroxypentanoate CoA transferase belonging to E.C. 2.8.3.14, a succinyl-CoA hydrolase belonging to E.C. 3.1.2.3, a 3-hydroxyisobutyryl-CoA hydrolase belonging to E.C. 3.1.2.4, an acyl-CoA hydrolase belonging to E.C. 3.1.2.20, or a 4-hydroxybenzoyl-CoA thioesterase belonging to E.C. 3.1.2.23; and
the enzyme that catalyzes reaction (J2) is a propionate CoA-transferase belonging to E.C. 2.8.3.1, a glutaconate CoA transferase belonging to E.C. 2.8.3.12, a 5-hydroxypentanoate CoA-transferase belonging to E.C. 2.8.3.14, an O-succinylbenzoate-CoA ligase (ADP-forming) belonging to E.C. 6.2.1.B1, a butyrate-CoA ligase belonging to E.C. 6.2.1.2, a glutarate-CoA ligase belonging to E.C. 6.2.1.6, a 4-coumarate-CoA ligase belonging to E.C. 6.2.1.12, a 6-carboxyhexanoate-CoA ligase belonging to E.C. 6.2.1.14, a dicarboxylate-CoA ligase belonging to E.C. 6.2.1.23, or a benzoate-CoA ligase belonging to E.C. 2.1.25; or
(K) alpha-aminopimelate to aminocaproic acid, wherein the enzyme that catalyzes reaction (K) is a benzoylformate decarboxylase belonging to E.C. 4.1.1.7, an aspartate 1-decarboxylase E.C. 4.1.1.11, a glutamate decarboxylase belonging to E.C. 4.1.1.15, an ornithine decarboxylase belonging to E.C. 4.1.1.17, a lysine decarboxylase belonging to E.C. 4.1.1.18, an arginine decarboxylase belonging to E.C. 4.1.1.19, a diaminopimelate decarboxylase belonging to E.C. 4.1.1.20, a tyrosine decarboxylase belonging to E.C. 4.1.1.25, an aromatic-L-amino-acid decarboxylase belonging to E.C. 4.1.1.28, or a diaminobutyrate decarboxylase belonging to E.C. 4.1.1.86.

3. The recombinant bacterial cell of claim 1, wherein the recombinant bacterial cell comprises at least one exogenous nucleic acid sequence encoding at least one enzyme that catalyzes a substrate to product conversion that is:

(I') (S)-1-amino-1-carboxy-2-hexenoyl-CoA to (S)-2-amino-5-heptenedioate, wherein the enzyme that catalyzes reaction (I') is a propionate CoA-transferase belonging to E.C. 2.8.3.1, a glutaconate CoA transferase belonging to E.C. 2.8.3.12, a 5-hydroxypentanoate CoA transferase belonging to E.C. 2.8.3.14, a succinyl-CoA hydrolase belonging to E.C. 3.1.2.3, a 3-hydroxyisobutyryl-CoA hydrolase belonging to E.C. 3.1.2.4, an acyl-CoA hydrolase belonging to E.C. 3.1.2.20, or a 4-hydroxybenzoyl-CoA thioesterase belonging to E.C. 3.1.2.23; or (I) (S)-2-amino-5-heptenedioate to (S)-1-amino-1-carboxy-2-hexenoyl-CoA, wherein the enzyme that catalyzes reaction (I) is a propionate CoA-transferase belonging to E.C. 2.8.3.1, a glutaconate CoA transferase belonging to E.C. 2.8.3.12, a 5-hydroxypentanoate CoA-transferase belonging to E.C. 2.8.3.14, an O-succinylbenzoate-CoA ligase (ADP-forming) belonging to E.C. 6.2.1.B1, a butyrate-CoA ligase belonging to E.C. 6.2.1.2, a glutarate-CoA ligase belonging to E.C. 6.2.1.6, a 4-coumarate-CoA ligase belonging to E.C. 6.2.1.12, a 6-carboxyhexanoate-CoA ligase belonging to E.C. 6.2.1.14, a dicarboxylate-CoA ligase belonging to E.C. 6.2.1.23, or a benzoate-CoA ligase belonging to E.C. 2.1.25.

4. The recombinant bacterial cell of claim 1, wherein the recombinant bacterial cell comprises at least one exogenous nucleic acid encoding at least one enzyme that catalyzes a substrate to product conversion comprising (C) (S)-2-amino-6-hydroxypimelate to (S)-2-amino-5-heptenedioate, wherein the enzyme that catalyzes reaction (C) is a dehydratase belonging to E.C. 4.2.1.X.

5. The recombinant bacterial cell of claim 1, wherein the recombinant bacterial cell comprises at least one exogenous nucleic acid encoding at least one enzyme that catalyzes a substrate to product conversion comprising (E) (S)-2-amino-5-heptenedioate to alpha-aminopimelate, wherein the enzyme that catalyzes reaction (E) is a fumarate reductase belonging to E.C. 1.3.1.6, a 2-enoate reductase belonging to E.C. 1.3.1.31, or a maleylacetate reductase belonging to E.C. 1.3.1.32.

* * * * *